United States Patent [19]

Yagi et al.

[11] Patent Number: 5,744,159
[45] Date of Patent: Apr. 28, 1998

US005744159A

[54] PLASMID ENTRAPPING MULTILAMELLAR LIPOSOMES

[75] Inventors: Kunio Yagi, Nagoya; Mariko Kitoh, Kani; Nobuko Ohishi, Inuyama, all of Japan

[73] Assignee: Institute of Applied Biochemistry Gifu-ken, Japan

[21] Appl. No.: 818,716

[22] Filed: Mar. 14, 1997

[51] Int. Cl.$^6$ .............. A61K 9/127; A61K 48/00; C12N 15/63

[52] U.S. Cl. .............. 424/450; 435/172.3; 435/320.1; 514/44

[58] Field of Search .............. 424/450; 514/44; 435/320.1, 172.3

[56] References Cited

U.S. PATENT DOCUMENTS 4,921,706  5/1990  Roberts et al. .............. 424/450
5,552,157  9/1996  Yagi et al. .............. 424/450

FOREIGN PATENT DOCUMENTS 2-135092  5/1990  Japan.
4-108391  4/1992  Japan.

*Primary Examiner*—Jasemine C. Chambers
*Assistant Examiner*—Scott D. Priebe
*Attorney, Agent, or Firm*—Nikaido, Marmelstein, Murray & Oram LLP

[57] ABSTRACT

A plasmid entrapping multilamellar liposome for introducing a gene into cells, which liposome has constitutive lipids of N-(α-trimethylammonioacetyl)-didodecyl-D-glutamate chloride (TMAG); dioctanoylphosphatidyl choline (DOPC) or didecanoylphosphatidyl choline (DDPC); and dioleoylphosphatidyl ethanolamine (DOPE) or dilauroylphosphatidyl ethanolamine (DLPE) and in a molar ratio of 1:2–3:2–1 in case of lipid combination of TMAG, DOPC and DOPE, or 1:2:2 in case of lipid combination of TMAG, DDPC or DOPC and DLPE.

2 Claims, 1 Drawing Sheet

●—● : Dilauroylphosphatidylethanolamine
▲—▲ : Didecanoylphosphatidylethanolamine 5,744,159

PLASMID ENTRAPPING MULTILAMELLAR LIPOSOMES

BACKGROUND OF THE INVENTION

1. Field of the Invention

The present invention relates to a plasmid entrapping multilamellar liposome, and more particularly to those containing as one of constitutive lipids a positively charged lipid of N-(α-trimethylammonioacetyl)-didodecyl-D-glutamate chloride (TMAG), showing higher plasmid entrapping efficiency and excellent efficiency in expression of a product by a transformed cell, and thus preferable in application thereof for a gene therapy.

2. Related Arts

The liposomes are small vesicles formed by two-molecule membrane of lipids and can entrap a substance in an inner water layer and membrane per se, and thus has a function as a carrier for introducing a various substance into a living body.

The technology has been developed to utilize the liposomes as a carrier for introducing a gene. The inventors have also reported that an addition of a positively charged lipid having quaternary amine is convenient for entrapping a gene in the liposomes, makes easy a preparation of multilamellar vesicles (MLV) and shows a low toxicity to cells [Jap. Pat. 2-135092(A) and 4-108391(A)].

The inventors had confirmed that such a multilamellar vesicle (MLV) can entrap a plasmid having an insert of a human interferon gene, which consists of constitutive lipids of N-(α-trimethylammonioacetyl)-didodecyl-D-glutamate chloride (TMAG), dilauroylphosphatidyl ethanolamine (DLPC) and dioleoylphosphatidyl ethanolamine (DOPE), that in case of introducing the liposomes which entrapped the human interferon gene into encephaloma cells, the tumor cells are inhibited in proliferation or killed, and that a certain remedy effect can be obtained in an animal test using encephaloma model mice. However, it has been still necessary to develop liposome preparations which show more excellent therapeutic effects to other tumor cells or excellent efficiency in expression of product by transformed cells.

In order to carry out a gene therapy by introducing a gene to cells, a relatively high stability is required on the liposomes as a carrier of the gene.

Incidentally, many of liposomes which have been used hitherto for introducing the gene contains as one of constitutive lipids DOPE having an unsaturated fatty acid in its side-chain and thus stabilization is required for elongating its storage period of time.

SUMMARY OF THE INVENTION

Therefore, an object of the invention lies in providing stabilized and plasmid entrapping liposomes which contain as one of constitutive lipids a positively charged lipid, show a good efficiency to introduce a gene entrapped therein to cells to be transformed by the gene, and show a high efficiency in expression of a product by the resulting transformed cells.

According to the invention, the object can be attained by a plasmid entrapping multilamellar liposome for introducing a gene, constitutive lipids of which are N-(α-trimethylammonioacetyl)-didodecyl-D-glutamate chloride (TMAG), dioctanoylphosphatidyl choline (DOPC) and dioleoylphosphatidyl ethanolamine (DOPE) and when TMAG occupies 20% of the total lipids, DOPC is 40–60% and the residual part is DOPE; or constitutive lipids of which are N-(α-trimethylammonioacetyl)-didodecyl-D-glutamate chloride (TMAG), didecanoylphosphatidyl choline (DDPC) or dioctanoylphosphatidyl choline (DOPC) and dilauroylphosphatidyl ethanolamine (DLPE) and when TMAG occupies 20% of the total lipids, DDPC or DOPC is 40% and the residual part is DLPE.

DETAILED DESCRIPTION OF THE PREFERRED EMBODIMENTS

Figure 1:
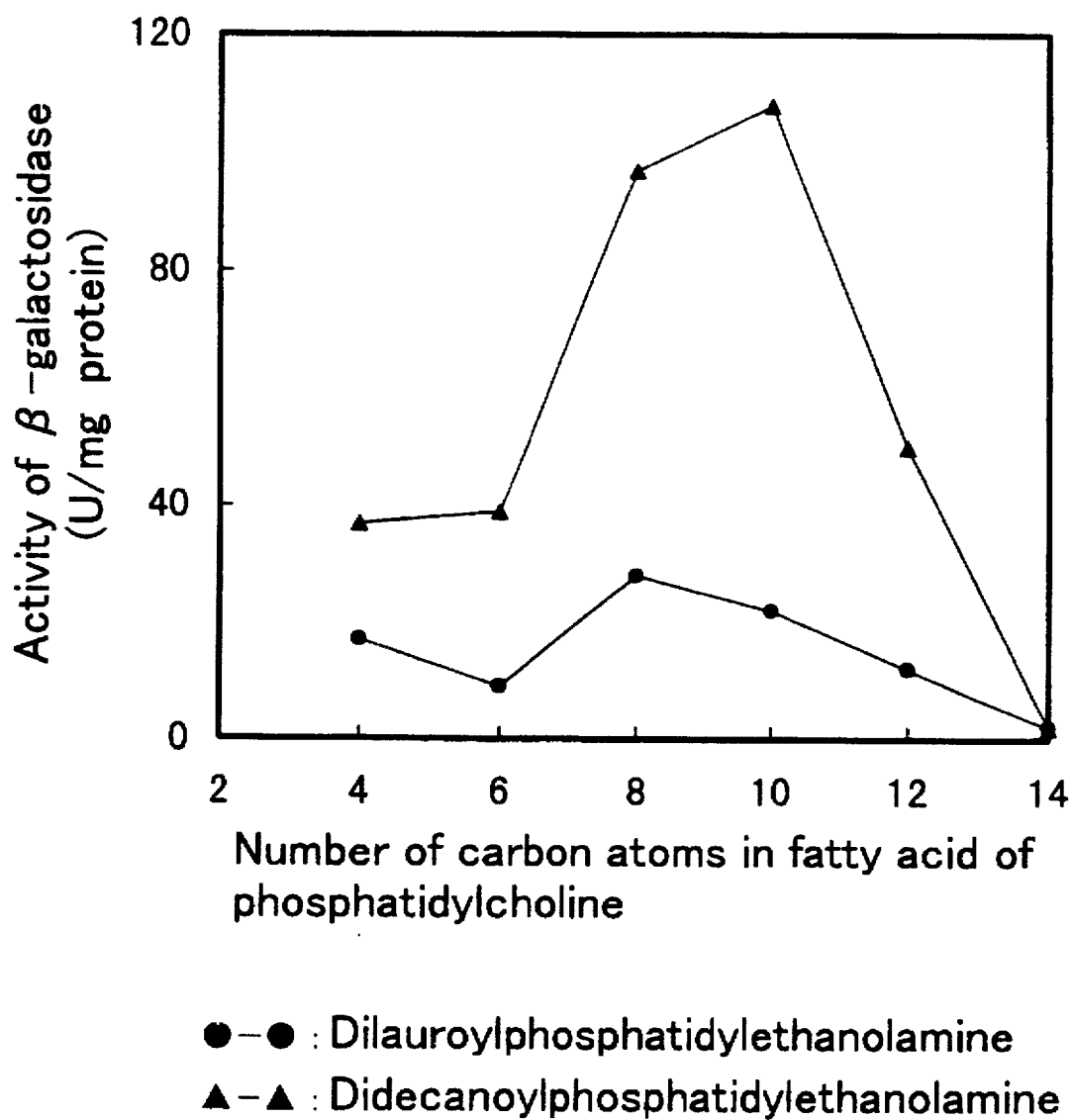
FIG. 1 is a graph showing results, in which an amount of β-galactosidase expressed by COS-1 cells was checked by measuring a specific activity of the enzyme, said cells were transformed by introducing pCH110 plasmid entrapping multilamellar liposomes therein, which liposomes have constitutive lipids of N-(α-trimethylammonioacetyl)-didodecyl-D-glutamate chloride (TMAG), a phosphatidyl choline which has at its side-chain a saturated fatty acid having carbon atoms of 4, 8, 10, 12 or 14, and a phosphatidyl ethanolamine which has at its side-chain a saturated fatty acid having carbon atoms of 10 or 12, and in a molar ratio of 1:2:2.

The invention will now be further explained with reference to Manufacturing Examples, Comparative Manufacturing Examples and Comparative Test Examples.

Following materials and testing methods have been selected for the Examples.

(a) N-(α-Trimethylammonioacetyl)-didodecyl-D-glutamate chloride (TMAG) marketed from Sougo Yakkou Kabushiki Kaisha of Japan.

(b) Dilauroylphosphatidyl choline (DLPC) and dioleoylphosphatidyl ethanolamine (DOPE) marketed from Nichiyu liposome Kabushiki Kaisha of Japan.

(c) Dioctanoylphophatidyl choline (DOPC), didecanoylphophatidyl choline (DDPC), dimyristoylphosphatidyl choline (DMPC), dihexanoylphosphatidyl choline (DHPC), dibutyrylphosphatidyl choline (DBPC), dilauroylphosphatidyl ethanolamine (DLPE), and didecanoylphosphatidyl ethanolamine (DDPE) marketed from Avanty Co., Ltd.

(d) pCH110 Plasmid marketed from Pharmacia Fine Chemicals AB of Uppsala, Sweden.

(e) COS-1 cell (CRL-1650 strain) marketed from Dainippon Pharmaceuticals. Co., Ltd. of Osaka, Japan.

(f) Method for preparing multilamellar liposomes: In accordance with the method disclosed in "Biochem. Biophys. Res. Commun.", Vol. 196, page 1042 (1993).

(g) Determination of β-galactosidase activity: In accordance with the method disclosed in "Experiments in Molecular Genetics", page 352 (1972), published from Cold Spring Harbor Inc.

(h) Determination of protein in cell extract: In accordance with the method disclosed in "Methods in Enzymology", Vol. 196, page 1042 (1993).

MANUFACTURING EXAMPLE 1

To a thin lipid film having constitutive lipids of TMAG, DOPC and DOPE in a molar ratio of 2:5:3, PBS (phosphate-buffered saline) containing pCH110 plasmid was added and stirred by a vortex mixer to prepare plasmid entrapping MLVs. In this case, 20 μg of plasmid DNA were added to 1 μmol of the total lipids.

COMPARATIVE MANUFACTURING EXAMPLE 1

By treating as described in Manufacturing Example 1 excepting that constitutive lipids are TMAG, DLPC and DOPE (a molar ratio of 1:2:2), pCH110 plasmid entrapping MLVs were prepared. Also in this case, 20 µg of plasmid DNA were added to 1 µmol of the total lipids.

COMPARATIVE TEST EXAMPLE 1

The pCH110 plasmid entrapping MLVs prepared by Manufacturing Example 1 or Comparative Manufacturing Example 1 were added to COS-1 cells to incubate for 16 hours. After having exchanged a medium with fresh one, the incubation was further continued for 2 days and then an activity of β-galactosidase expressed in the cells was measured.

As apparently seen from results shown in following Table 1, an expression efficiency of product by the transformed cells is 6-fold higher, when the plasmid entrapping liposomes prepared by Manufacturing Example 1 and using as one of constitutive lipids DOPC which has at its side-chain octanoyl radical having 8 carbon atoms, in comparison with the plasmid entrapping liposomes prepared by Comparative Manufacturing Example 1 and using as one of constitutive lipids DLPC which has at its side-chain lauroyl radical having 12 carbon atoms.

TABLE 1

| Test compounds | Activity of β-galactosidase (U/mg protein) |
| --- | --- |
| Example 1 | 122 |
| Comparative Example 1 | 21 |

Similar results were obtained by an activity staining test of the cells using X-gal reagent.

From the above facts, it has been confirmed that the liposomes according to the present invention provide an excellent efficiency in expression of a product by transformed cells.

MANUFACTURING EXAMPLE 2

To a thin lipid film which has constitutive lipids of TMAG, a phosphatidyl choline having at its side-chain a saturated fatty acid having carbon atoms of 4, 8, 10, 12 or 14, and DLPE having at side-chain a saturated fatty acid having 12 carbon atoms (a molar ratio of 1:2:2), PBS (phosphate-buffered saline) containing pCH110 plasmid was added and stirred by a vortex mixer to prepare plasmid entrapping MLVs. In this case, 20 µg of plasmid DNA were added to 1 µmol of the total lipids.

COMPARATIVE MANUFACTURING EXAMPLE 2

Plasmid entrapping MLVs were prepared by treating as described in Manufacturing Example 2 excepting that as constitutive lipids of TMAG, a phosphatidyl choline having at its side-chain a saturated fatty acid having carbon atoms of 4, 8, 10, 12 or 14, and DDPE having as its side-chain a saturated fatty acid having 10 carbon atoms were selected (a molar ratio of 1:2:2). Also in this case, 20 µg of plasmid DNA was added to 1 µmol of the total lipids.

COMPARATIVE TEST EXAMPLE 2

The pCH110 plasmid entrapping MLVs prepared by Manufacturing Example 2 or Comparative Manufacturing Example 2 were added to COS-1 cells to incubate for 16 hours. After having exchanged a medium with fresh one, the incubation was further continued for 2 days and then an activity of β-galactosidase expressed in the transformed cells was measured.

As apparently seen from results shown in FIG. 1, an expression efficiency of product by the transformed cells is 4-fold higher, when the plasmid entrapping liposomes prepared by Manufacturing Example 2 and using as one of constitutive lipids DOPC which has at its side-chain octanoyl radical having 8 carbon atoms or DDPC which has at its side-chain decanoyl radical having 10 carbon atoms, in comparison with the plasmid entrapping liposomes prepared by Comparative Manufacturing Example 2.

Similar results were also obtained by an activity staining test of the cells using X-gal reagent.

From the above facts, it has been confirmed that the liposomes according to the invention provide an excellent efficiency in expression of a product by transformed cells.

What is claimed is:

1. A multilamellar liposome for entrapping plasmids which comprises lipids of N-(α-trimethylammonioacetyl)-didodecyl-D-glutamate chloride (TMAG), dioctanoylphosphatidyl choline (DOPC), and dioleoylphosphatidyl ethanolamine (DOPE) and wherein TMAG occupies 20% mole fraction of the total lipids, DOPC is 40–60% mole fraction and DOPE is 20–40% mole fraction.

2. A multilamellar liposome for entrapping plasmids which comprises lipids of N-(α-trimethylammonioacetyl)-didodecyl-D-glutamate chloride (TMAG), didecanoylphosphatidyl choline (DDPC) or dioctanoylphosphatidyl choline (DOPC) and dilauroylphosphatidyl ethanolamine (DLPE) and wherein TMAG occupies 20% mole fraction of the total lipids, DDPC or DOPC is 40% mole fraction and the residual part is DLPE, is 40% mole fraction.

\* \* \* \* \*